Figure 2:
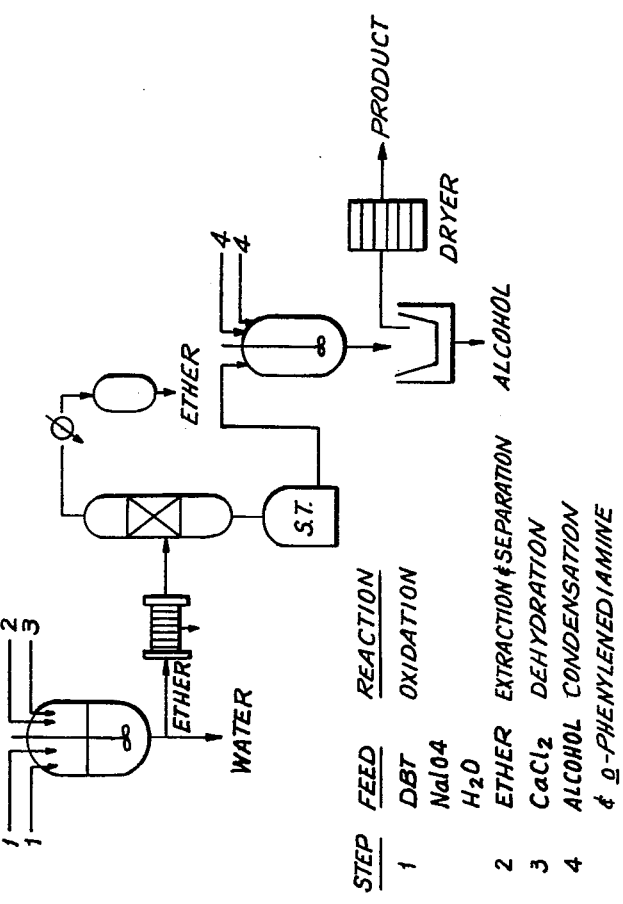

United States Patent [19]

Su et al.

[11] 4,450,271

[45] May 22, 1984

[54] PREPARATION OF 2-HYDROXYQUINOXALINE

[75] Inventors: Tsung-Tsan Su; Yu-Chen Cheng, both of Hsinchu, Taiwan

[73] Assignee: Industrial Technology Research Institute, Hsinchu, Taiwan

[21] Appl. No.: 399,275

[22] Filed: Jul. 19, 1982

[51] Int. Cl.$^3$ .......................................... C07D 241/44
[52] U.S. Cl. ................................................... 544/354
[58] Field of Search ......................................... 544/354

[56] References Cited

U.S. PATENT DOCUMENTS 4,262,123  4/1981  Hall et al. ........................... 544/354

OTHER PUBLICATIONS

Cheeseman, G. W. H., J. Chem. Soc., 3236, (1957), Chem. Abs. 90,104008h, 87, 184459g.

Primary Examiner—Mark L. Berch
Assistant Examiner—Chabi C. Kalita
Attorney, Agent, or Firm—Andrew D. Maslow

[57] ABSTRACT

An improved procedure for the manufacture of 2-hydroxyquinoxalines from reacting a dialkyl tartrate with a periodate, adjusting the pH of the resulting reaction mixture, and condensing said mixture with an o-phenylenediamine.

3 Claims, 2 Drawing Figures

PREPARATION OF 2-HYDROXYQUINOXALINE

This invention relates to an improved method for the manufacture of 2-hydroxyquinoxalines. More particularly, it concerns the addition of o-phenylenediamines under controlled conditions to the reaction mixture of dialkyl tartrates and periodates to produce 2-hydroxyquinoxalines in high yields.

In the prior art Gowenlock et al, *J. Chem. Soc.*, pp 622-625 (1945) disclose the condensation of o-phenylenediamine with ethyl glyoxylate, and the decarboxylation of 2-hydroxyquinoxaline-3-carboxylic acid to yield 2-hydroxyquinoxaline.

U.S. Pat. No. 2,537,871 to Wolf discloses the reaction of o-phenylenediamine with glyoxalic acid, a lower alkyl glyoxalate, or the addition product of glyoxalic acid and sodium bisulfite to form 2-hydroxyquinoxaline. A mixture of o-phenylene diamine and the second reactant in 100 ml of water was stirred for 15 minutes and then heated at 50° C. for 15 minutes. The precipitate was taken up to 100 ml of 1.0 N NaOH, treated with decolorizing charcoal, and the product reprecipitated by acidification with acetic acid.

U.S. Pat. No. 3,928,350 to Nottke discloses a process for making 3-substituted 2-hydroxyquinoxalines by the reaction of o-arylenediamines with trihalovinyl epoxides. The production of 2-hydroxyquinoxaline is discussed at Column 1, lines 17-29.

U.S. Pat. No. 4,262,123 to Hall et al disclose compounds of the quinoxalinone family and 2-hydroxyquinoxaline (see column 1, lines 46-59).

The well-known procedure such as that described in J. Chem. Soc., 26(1956), 3236(1957) for the production of 2-hydroxyquinoxaline from dialkyl tartrate, periodate, and o-phenylenediamines comprises the reaction of dialkyl tartrates with a periodate and condensing the resulting alkyl glyoxylates with o-phenylenediamines. (other related procedures are mentioned in J. Chem. Soc., 622-5, 1945; J. Am. Chem. Soc., v.73, 3246-7, 1951; J. Am. Chem. Soc., v.76 4483, 1954; J. Org. Chem., v.26, 945-6, 1961).

In the above prior art the isolation of alkyl glyoxylate, involves extraction, separation, drying, and concentration steps. It is known that alkyl glyoxlate of the processes of the above prior art undergoes autoxidation and should be stored under nitrogen or it can cause relatively large and undesirable changes. As a result, it will effect both yield and quality of the 2-hydroxyquinoxalines isolated.

It is therefore the object of the present invention to provide an improved process to avoid above-mentioned disadvantages. In the embodiment, the process of the present invention is characterized by adjusting the pH of the reaction mixture of dialkyl tartrates and a periodate to pH of 6-7 followed by the addition of o-phenylenediamines to form 2-hydroxyquinoxalines in quantitative yield.

A feature of the present invention is to combine the oxidation and condensation reaction in a one-step reaction. Also important is that the isolation of alkyl glyoxylate is avoided. This not only can save the steps of extraction, separation, drying, and concentration, which are necessary if the isolation of alkyl glyoxylate is mandatory, but also solve the storage problem of alkyl glyoxylate. Therefore, the present invention is a commercially practical process.

Figure 1:
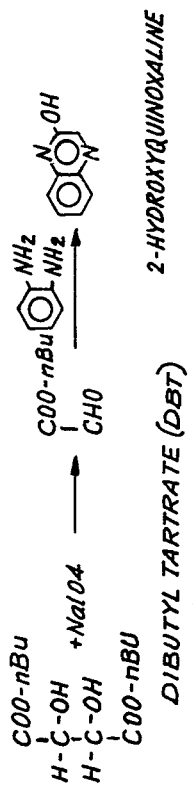

FIG. 1 is a schematic diagram which shows the traditional process for preparing 2-hydroxyquinoxaline as compared to the instant improved process shown schematically in FIG. 2.

In general, the process of the present invention comprises the steps of reacting dialkyl tartrates with a periodate, adjusting pH of the resulting reaction mixture to 6-7, and condensing said mixture with o-phenylenediamines.

The aforementioned reactions are carried out at temperature ranging from 15°-80° C. Water is a preferred solvent for both oxidation and condensation from the economical point of view. However organic solvents can also be used.

The present invention is further described by the following illustrative examples, which are not to be construed in any way as limiting the spirit or scope of the invention. Relative amounts of material are given in parts by weight unless otherwise indicated.

EXAMPLE 1 o-phenylenediamine (43.2 parts) was added to a neutral solution (pH of 6-7) of butyl glyoxylate, which was prepared from dibutyl tartrate (52.4 parts), sodium periodate (42.8 parts), water (500 ml) followed by adjusting pH of the reaction mixture with 1 N NaOH aq. solution. The mixture was stirred for 15 min., heated to 50° C. for 15 min., the product was then filtered off, washed with water, and dried. Yield, 100%. The crude product was taken up with 1 N NaOH (250 ml), charcoaled, and reprecipitated by acidification with acetic acid (or 20% aq. HCl) to give 55.5 parts (95%) of 2-hydroxyquionxaline; mp 268°-269° C.

EXAMPLE 2

By a process similar to that of Example 1, using 26.4 parts of dibutyl tartrate, 23 parts of potassium periodate, 700 ml of water, and 21.6 parts of o-phenylenediamine, crude yield of 2-hydroxyquinoxaline was 100%.

EXAMPLE 3 o-phenylenediamine (2.16 parts) was added to a neutral solution pH of 6-7 of butyl glyoxylate which was prepared from dibutyl tartrate (2.62 parts), sodium periodate (2.14 parts), and water (25 ml) followed by adjusting pH of the reaction mixture with 1 N NaOH aq. solution. The mixture was stirred for 3 hr. at room temperature. The product was then filtered off, washed with water and dried; yield, 100%. The crude product was purified by the procedure described in Example 1; yield, 72%; mp 269° C.

EXAMPLE 4 o-phenylenediamine (2.16 parts) was added to a slightly acidic solution (pH=5-6) of butyl glyoxylate, prepared from dibutyl tartrate (2.64 parts), sodium periodate (2.15 parts), and water (25 ml) followed by adjusting pH of the reaction mixture with 1 N NaOH aq. solution. The mixture was stirred for 15 min., heated to 50° C. for 15 min., the product was then treated as described in Example 1; yield, 67%; mp 269°-272° C.

EXAMPLE 5

By a process similar to that of Example 4, the pH of the butyl glyoxylate solution was adjusted to 9. The yield of 2-hydroxyquinoxaline was 23%; mp 269°-272° C.

We claim:

1. A process for preparing 2-hydroxyquinoxalines comprising the steps of reacting a dialkyl tartrate with a periodate, adjusting the pH of the resulting reaction mixture to 6–7, and condensing said mixture with an o-phenylenediamine.

2. The method of claim 1 wherein said dialkyl tartrate is dibutyl tartrate.

3. The method of claim 1 wherein said periodate is sodium periodate or potassium periodate.

* * * * *